(12) United States Patent
Salter et al.

(10) Patent No.: US 11,608,004 B2
(45) Date of Patent: Mar. 21, 2023

(54) STORAGE BIN FOR VEHICLE DOOR

(71) Applicant: Ford Global Technologies, LLC, Dearborn, MI (US)

(72) Inventors: Stuart C. Salter, White Lake, MI (US); Aaron Gould, Detroit, MI (US); David Brian Glickman, Southfield, MI (US); Paul Kenneth Dellock, Northville, MI (US); Marguerite Kimball, Brighton, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 380 days.

(21) Appl. No.: 17/001,730

(22) Filed: Aug. 25, 2020

(65) Prior Publication Data

US 2022/0063505 A1    Mar. 3, 2022

(51) Int. Cl.
| | |
|---|---|
| *B60R 7/04* | (2006.01) |
| *B60J 5/04* | (2006.01) |
| *B60Q 3/80* | (2017.01) |
| *B60Q 3/68* | (2017.01) |
| *B60Q 3/225* | (2017.01) |
| *A61L 2/26* | (2006.01) |
| *H05B 47/115* | (2020.01) |
| *A61L 2/08* | (2006.01) |
| *H05K 1/18* | (2006.01) |

(52) U.S. Cl.
CPC .............. *B60R 7/046* (2013.01); *A61L 2/088* (2013.01); *A61L 2/26* (2013.01); *B60J 5/0493* (2013.01); *B60Q 3/225* (2017.02); *B60Q 3/68* (2017.02); *B60Q 3/80* (2017.02); *H05B 47/115* (2020.01); *A61L 2202/11* (2013.01); *A61L 2202/14* (2013.01); *A61L 2202/23* (2013.01); *H05K 1/181* (2013.01); *H05K 2201/10151* (2013.01)

(58) Field of Classification Search
CPC .......... B60R 7/046; B60Q 3/225; B60Q 3/80; B60Q 3/68; H05B 47/115; A61L 2/088; A61L 2/26; A61L 2202/11; A61L 2202/14; A61L 2202/23; B60J 5/0493; H05K 1/181; H05K 2201/10151
See application file for complete search history.

(56) References Cited

U.S. PATENT DOCUMENTS

| | | | |
|---|---|---|---|
| 5,800,004 A * | 9/1998 | Ackeret | ................... B60R 7/12 296/37.13 |
| 5,895,086 A * | 4/1999 | Carico | ................... B60R 11/06 296/37.6 |
| 7,086,689 B2 | 8/2006 | Dean | |

(Continued)

FOREIGN PATENT DOCUMENTS

| | | |
|---|---|---|
| EP | 3498536 A1 | 6/2019 |
| JP | H0685137 U | 12/1994 |
| KR | 20150066139 A | 6/2015 |

*Primary Examiner* — Bao Q Truong
(74) *Attorney, Agent, or Firm* — Vichit Chea; Carlson, Gaskey & Olds, P.C.

(57) ABSTRACT

This disclosure relates to storage bin for a door of a motor vehicle. In an example, a door, which provides a boundary between a passenger compartment of the motor vehicle and an exterior of the motor vehicle, includes a storage bin configured such that an item in the storage bin is accessible both from the passenger compartment and from the exterior.

20 Claims, 5 Drawing Sheets

(56) References Cited

U.S. PATENT DOCUMENTS

| | | | |
|---|---|---|---|
| 9,016,748 B1* | 4/2015 | Ardigo | B60R 7/046 |
| | | | 296/37.13 |
| 2015/0217683 A1* | 8/2015 | Salter | B60Q 3/68 |
| | | | 362/546 |
| 2017/0091711 A1 | 3/2017 | Akselrod et al. | |

* cited by examiner

STORAGE BIN FOR VEHICLE DOOR

TECHNICAL FIELD

This disclosure relates to a storage bin for a door of a motor vehicle.

BACKGROUND

Motor vehicles are known to include doors, which are configured to selectively open and close to uncover and cover openings in a body of the vehicle. When open, doors permit the driver and/or passengers of the vehicle to enter or exit the passenger compartment of the vehicle. When closed, the doors provide a barrier between the passenger compartment and the exterior of the vehicle.

SUMMARY

A motor vehicle according to an exemplary aspect of the present disclosure includes, among other things, a door providing a boundary between a passenger compartment of the motor vehicle and an exterior of the motor vehicle. Further, the door includes a storage bin configured such that an item in the storage bin is accessible both from the passenger compartment and from the exterior.

In a further non-limiting embodiment of the foregoing motor vehicle, the door includes an inner panel and an outer panel spaced-apart from the inner panel, and the storage bin is at least partially between the inner panel and the outer panel.

In a further non-limiting embodiment of any of the foregoing motor vehicles, the storage bin includes a reinforcement assembly between the inner panel and the outer panel.

In a further non-limiting embodiment of any of the foregoing motor vehicles, the reinforcement assembly includes: a bottom wall extending between the inner panel and the outer panel, a top wall spaced-apart from the bottom wall and extending between the inner panel and the outer panel, a forward wall extending between the inner panel and the outer panel and further extending between the bottom wall and the top wall, and a rear wall spaced-apart from the forward wall and extending between the inner panel and the outer panel and further extending between the bottom wall and the top wall.

In a further non-limiting embodiment of any of the foregoing motor vehicles, the bottom wall, top wall, forward wall, and rear wall are provided by a single, integrally-formed assembly.

In a further non-limiting embodiment of any of the foregoing motor vehicles, the inner panel includes an opening leading to the storage bin, and the outer panel includes an opening leading to the storage bin.

In a further non-limiting embodiment of any of the foregoing motor vehicles, the opening of the outer panel is at least partially aligned with the opening of the inner panel.

In a further non-limiting embodiment of any of the foregoing motor vehicles, the storage bin includes an inner cover moveable relative to the door to selectively cover and uncover the opening of the inner panel, and the storage bin includes an outer cover moveable relative to the door to selectively cover and uncover the opening of the outer panel.

In a further non-limiting embodiment of any of the foregoing motor vehicles, the inner cover is biased toward a closed position in which the inner cover covers the opening of the inner panel by a first biasing member, and the outer cover is biased toward a closed position in which the outer cover covers the opening of the outer panel by a second biasing member.

In a further non-limiting embodiment of any of the foregoing motor vehicles, the vehicle includes a lock configured to selectively lock the outer cover in the closed position.

In a further non-limiting embodiment of any of the foregoing motor vehicles, the inner cover is at least partially made of a transparent material such that contents of the storage bin are visible from the passenger compartment.

In a further non-limiting embodiment of any of the foregoing motor vehicles, the inner cover includes a sound absorbing panel, and the outer cover includes a sound absorbing panel.

In a further non-limiting embodiment of any of the foregoing motor vehicles, the vehicle includes an ultraviolet (UV) light source configured to emit UV light within the storage bin to disinfect an item within the storage bin.

In a further non-limiting embodiment of any of the foregoing motor vehicles, the vehicle includes a controller configured to issue a command to the UV light source to selectively cause the UV light source to emit UV light.

In a further non-limiting embodiment of any of the foregoing motor vehicles, the controller is in communication with a sensor configured to generate a signal indicative of whether an item is present in the storage bin and is further configured to command the UV light source to emit UV light for a period of time following detection of an item in the storage bin.

In a further non-limiting embodiment of any of the foregoing motor vehicles, the controller is further configured to transmit a message indicative of one or both whether an item is present in the storage bin and whether the UV light has been activated for the period of time.

In a further non-limiting embodiment of any of the foregoing motor vehicles, the vehicle includes a printed circuit board mounted to the door adjacent the storage bin. Further, the sensor, controller, and UV light source are mounted to the printed circuit board.

A method according to an exemplary aspect of the present disclosure includes, among other things, placing an item in a storage bin of a door of a motor vehicle by accessing the storage bin from an exterior of the motor vehicle, and transmitting a message indicating an item is in the storage bin.

In a further non-limiting embodiment of the foregoing method, the method includes sanitizing the item using UV light, and retrieving the item, after the sanitizing step, from the storage bin by accessing the storage bin from a passenger compartment of the motor vehicle.

In a further non-limiting embodiment of any of the foregoing methods, after the sanitizing step and before the retrieving step, the message indicates that a sanitization process has completed.

BRIEF DESCRIPTION OF THE DRAWINGS

In FIG. 3, inner and outer covers of the storage bin are in a closed position.

In FIG. 4, the inner and outer cover of the storage bin are not illustrated for reference.

DETAILED DESCRIPTION

This disclosure relates to storage bin for a door of a motor vehicle. In an example, a door, which provides a boundary between a passenger compartment of the motor vehicle and an exterior of the motor vehicle, includes a storage bin configured such that an item in the storage bin is accessible both from the passenger compartment and from the exterior. The storage bin permits a user to arrange for a delivery or schedule a pickup of an item via the storage bin in their vehicle door. The storage bin provides for increased security, cleanliness, and ease of use, among other benefits, which will be appreciated from the below description.

Figure 1:
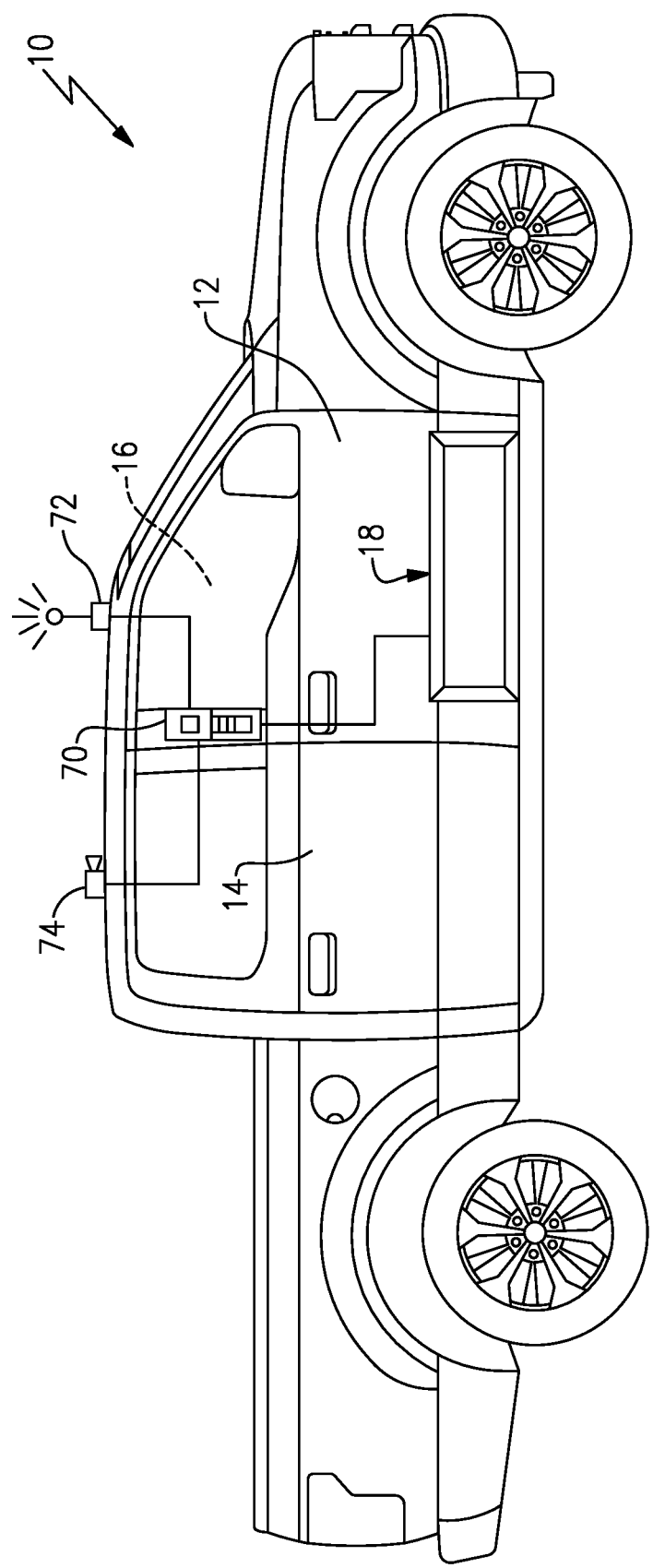
FIG. 1 is a side view of an exemplary motor vehicle.

Referring to the drawings, FIG. 1 is a side view of a motor vehicle 10 ("vehicle 10"), and in particular illustrates the passenger side of the vehicle 10. The vehicle 10 in this example is a pickup truck. This disclosure extends to other types of vehicles including cars, sport utility vehicles (SUVs), vans, etc. Further, while a four door vehicle is shown in FIG. 1, this disclosure extends to vehicles having one or more doors.

FIG. 1 illustrates a front passenger door 12 and a rear passenger door 14. Each of the doors 12, 14 are configured to selectively open and close relative to a body assembly of the vehicle 10 via a hinged connection. When open, the doors 12, 14 permit users to enter and exit a passenger compartment 16, or passenger cabin, of the vehicle 10. When closed, the doors 12, 14 provide a boundary between the passenger compartment 16 and the exterior of the vehicle 10.

In FIG. 1, the door 12 includes a storage bin 18. The storage bin 18 is an assembly configured to receive and contain one or more items. The storage bin 18, in this example, is accessible both from the passenger compartment 16 and from the exterior of the vehicle 10. In this way, items such as packages can be delivered directly to the vehicle 10 via the storage bin 18 from a person, such as a delivery person, at the exterior of the vehicle 10 and retrieved by another person in the passenger compartment 16.

While only one storage bin is shown in FIG. 1, other doors of the vehicle 10, including the door 14 and the doors on the driver side of the vehicle 10, could include similar storage bins. Further, the storage bin 18 could be incorporated into other areas of the vehicle 10, such as the cargo area of the vehicle 10, including the side walls and/or tailgate of the vehicle 10. That said, this disclosure has particular benefits in the context of storage bins provided in doors leading to the passenger compartment.

FIGS. 2-5 illustrate the door 12 and the storage bin 18 from various views without the remainder of the vehicle 10 for ease of reference. The door 12 includes an inner panel 20 generally facing the passenger compartment 16 and an outer panel 22 facing the exterior of the vehicle 10 and spaced-apart from the inner panel 20 by an interior space 24. The storage bin 18 is arranged at least partially between the inner panel 20 and outer panel 22. Namely, the storage bin 18 is arranged at least partially in the interior space 24.

The door 12 includes a pass-through opening 26, in this example, which is arranged about an axis A. The pass-through opening 26 is configured such that items, such as packages, may be fit into the pass-through opening 26 and be retrieved out of the pass-through opening 26 such that those items can be passed through the door 12 via the pass-through opening 26. The pass-through openings 26 passes completely through the door 12. When the door 12 is closed, the axis A is substantially perpendicular to a centerline of the vehicle 10. The pass-through opening 26 is provided by an opening 28 in the inner panel 20 and an opening 30 in the outer panel 22. The openings 28, 30 are at least partially aligned in this example. In particular, the openings 28, 30 are both arranged about the axis A and are aligned such that when the pass-through opening 26 is viewed along the axis A, the openings 28, 30 appear to overlap one another. In this regard, the openings 28, 30 are substantially the same size and shape in one example.

The pass-through opening 26 is located such that it does not interfere with normal operation of the window, namely the normal travel of the glass of the window as the window opens and closes. In this example, the pass-through opening 26 is arranged such that the upper edge of the pass-through opening 26 is at a first height $H_1$ below the window opening W. Further, the bottom edge of the pass-through opening 26 is arranged at a second height $H_2$ above a ground surface G such that the pass-through opening 26 is conveniently accessed by delivery personnel, for example.

In order to securely hold items in the pass-through opening 26, the storage bin 18 includes a reinforcement assembly 32 and inner and outer covers (i.e., inner and outer doors) 34, 36, each of which will now be described in turn.

In this example, the reinforcement assembly 32 is arranged between the inner panel 20 and the outer panel 22 and is configured to support items in the storage bin 18, specifically items within the pass-through opening 26 that would have otherwise fallen into or become lodged in the interior space 24. The reinforcement assembly 32 in this example includes a bottom wall 38 extending between the inner panel 20 and the outer panel 22 in a direction parallel to the axis A. The reinforcement assembly 32 further includes a top wall 40 spaced-apart vertically (i.e., in the up-and-down direction) from the bottom wall 38, and further extending between the inner panel 20 and the outer panel 22. The reinforcement assembly 32 also includes a forward wall 42 extending between the inner panel 20 and the outer panel 22, and further extending vertically between the bottom wall 38 and the top wall 40. At a rearward location, the reinforcement assembly 32 includes a rear wall 44 spaced-apart from the forward wall 42 and extending between the inner panel 20 and the outer panel 22, and further extending between the bottom wall 38 and the top wall 40. The terms "forward" and "rearward"/"rear" refer generally to the normal orientation of the vehicle 10 and the door 12, namely forward is in the right-hand direction in FIG. 4 and rearward is in the left-hand direction in FIG. 4.

In an example, the bottom wall 38, top wall 40, forward wall 42, and rear wall 44 are provided by a single, integrally-formed assembly generally resembling a ring or hoop. Alternatively, the bottom wall 38, top wall 40, forward wall 42, and rear wall 44 are provided by separate, individual walls. The reinforcement assembly 32 may be attached to the inner and outer panels 20, 22 by welding or another known attachment technique. If by welding, the bottom wall 38, top wall 40, forward wall 42, and rear wall 44 may include flanges at edges thereof to facilitate welding the walls to the inner and outer panels 20, 22. The reinforcement assembly 32, namely the bottom wall 38, provides an effective support for items in the storage bin 18, and the reinforcement assembly 32 further provides an air and water tight seal between the interior space 24 and the pass-through opening 26 such that items in the storage bin 18 remain dry. To this end, while in some figures certain portions of the reinforcement assembly 32 are shown with a slight gap or space between the inner and/or outer panels 20, 22, in most embodiments the reinforcement assembly 32 is in contact with the inner and outer panels 20, 22 either directly or indirectly via a seal or weld bead, as examples, such that there are no such gaps or spaces.

In order to selectively permit and restrict access to the storage bin 18, the storage bin 18 includes an inner cover 34 moveable relative to the door 12 to selectively cover and uncover the opening 28 of the inner panel 20, and an outer cover 36 moveable relative to the door 12 to selectively cover and uncover the opening 30 of the outer panel 22. In an example, the inner cover 34 is made at least partially made of a transparent material, such as clear plastic, such that contents of the storage bin are visible from the passenger compartment. In this example, the outer cover 36 is fully opaque such that the contents of the storage bin 18 are not visible from the exterior of the vehicle 10. The inner and outer covers 34, 36 may be made of other materials in other examples.

Figure 2:
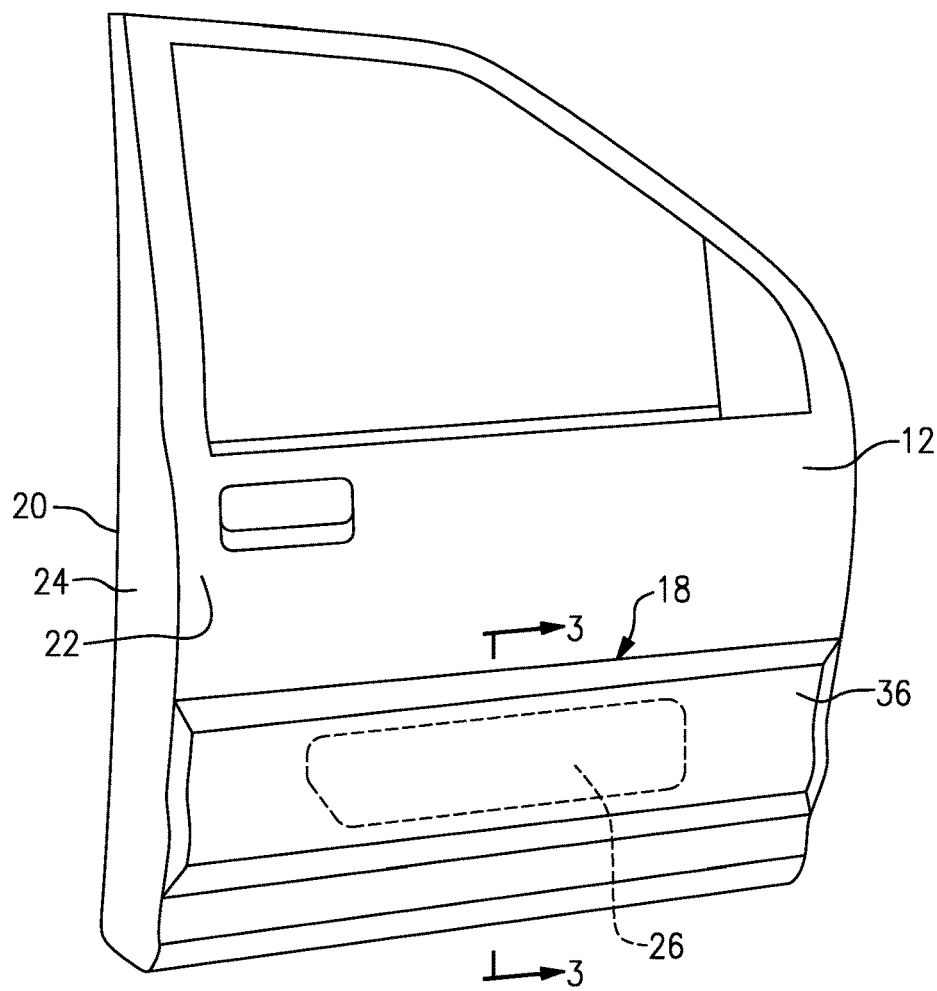
FIG. 2 is a side perspective view of a vehicle door including an example storage bin.
Figure 3:
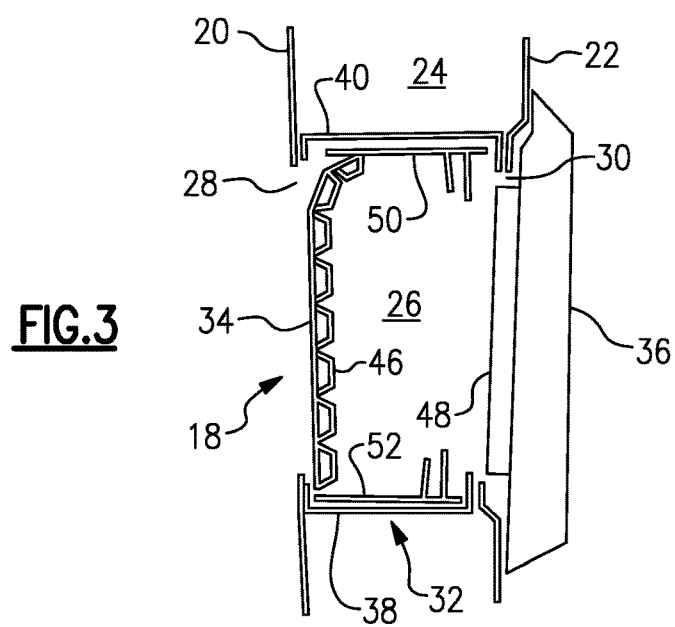
FIG. 3 is a cross-sectional view taken along line 3-3 from FIG. 2 and illustrates additional detail of the example storage bin.
Figure 4:
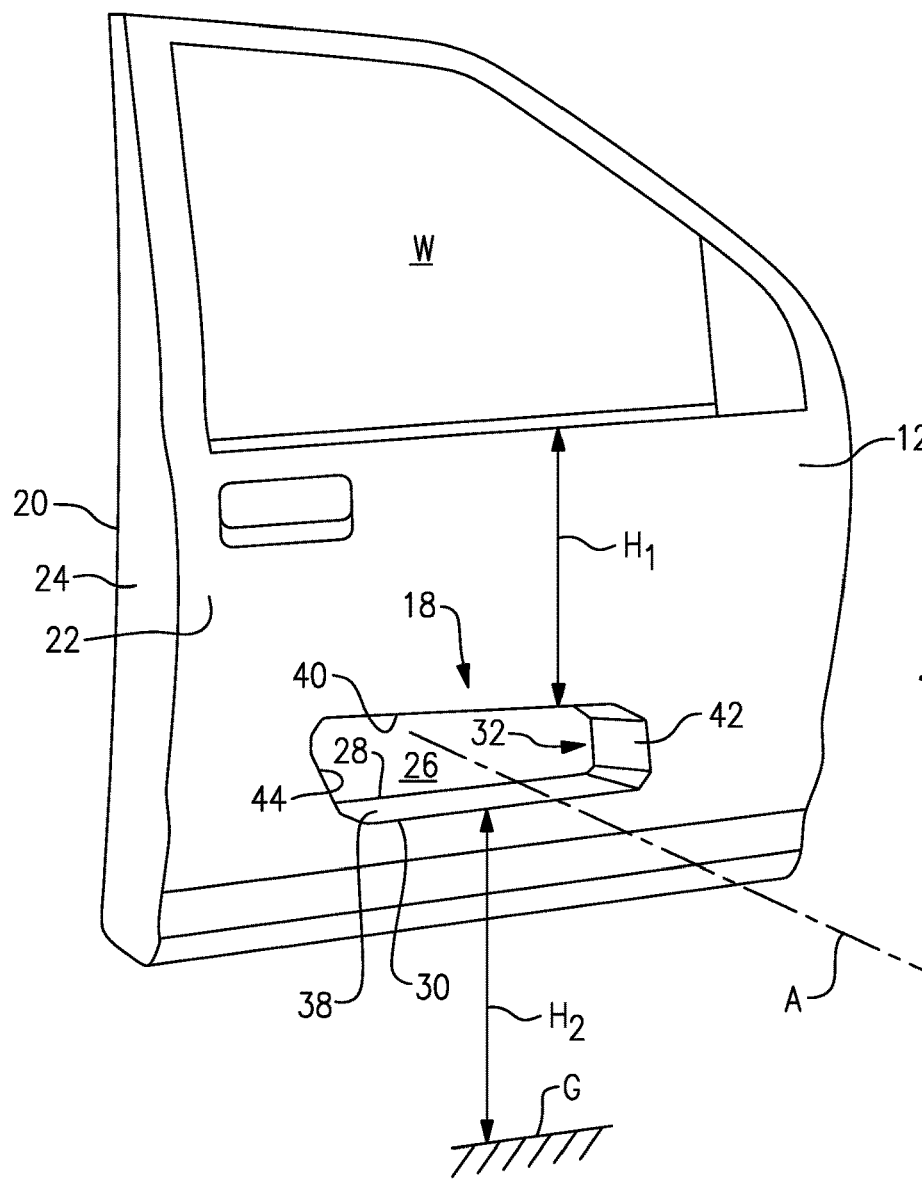
FIG. 4 is a side perspective view of the vehicle door of FIG. 2, and illustrates a pass-through opening of the vehicle door.
Figure 5:
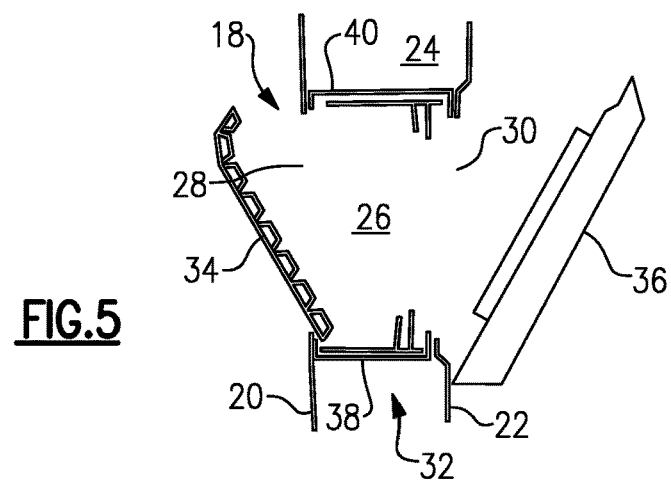
FIG. 5 is a cross-sectional view similar to FIG. 3 but with the inner and outer covers of the storage bin in an open position.

The inner and outer covers 34, 36 are in a closed position in FIGS. 2-4 and in an open position in FIG. 5. In this example, the inner cover 34 and the outer cover 36 are flaps which are hingedly connected to the door 12 adjacent a bottom edge of the pass-through opening 26. The inner and outer covers 34, 36 could be connected to the door 12 in a manner other than by a hinged connection, such as by a sliding connection. In the example of FIGS. 2-5, the inner and outer covers 34, 36 generally lie in a vertical plane, parallel to the direction of the force due to gravity, in the closed position and are rotatable away from the door 12 to a respective open position. The inner and outer covers 34, 36 are biased to the closed position, in this example, by a respective first and second biasing member, such as a coil springs or another known type of biasing member.

The inner cover 34, in this example, is configured to fit in the pass-through opening 26 when in the closed position. The outer cover 36, in this example, is sized larger than the area of the pass-through opening 26 and is shaped such that the outer cover 36 surrounds the pass-through opening about the entire perimeter of the pass-through opening 26 when the outer cover 36 is in the closed position. As shown, when closed, the outer cover 36 abuts the outer panel 22. When closed, the outer cover 36 is configured to provide an air and water tight seal relative to the outer panel 22 to protect the items in the storage bin 18 from environmental conditions and chance opportunists that may attempt to access the storage bin 18 without permission.

An aspect of this disclosure relates to sound absorption (i.e., noise attenuation). In this aspect of the disclosure, one or more portions of the storage bin 18 are fitted with sound absorbing panels. Such panels are known and are made of material configured to suppress or attenuate noise. In the example of FIG. 4, a first sound absorbing panel 46 is arranged on an inner surface (i.e., the surface facing the outer cover 36) of the inner cover 34. Further, a second sound absorbing panel 48 is arranged on an inner surface (i.e., the surface facing the inner cover 34) of the outer cover 36. The sound absorbing panels 46, 48 are mounted to the inner and outer covers 34, 36 such that they are moveable with movement of the respective inner and outer cover 34, 36. The reinforcing assembly 32 further includes one or more trim pieces configured to absorb sound. In particular, in this example, an upper sound absorbing trim piece 50 is mounted to the top wall 40 and a lower sound absorbing trim piece 52 is mounted to the bottom wall 38. The sound absorbing trim pieces 50, 52 are fixed and non-moveable in this example. The sound absorbing panels 46, 48 and trim pieces 50, 52 may include at least one baffle. While one particular noise attenuation arrangement is shown, other arrangements come within the scope of this disclosure.

Figure 6:
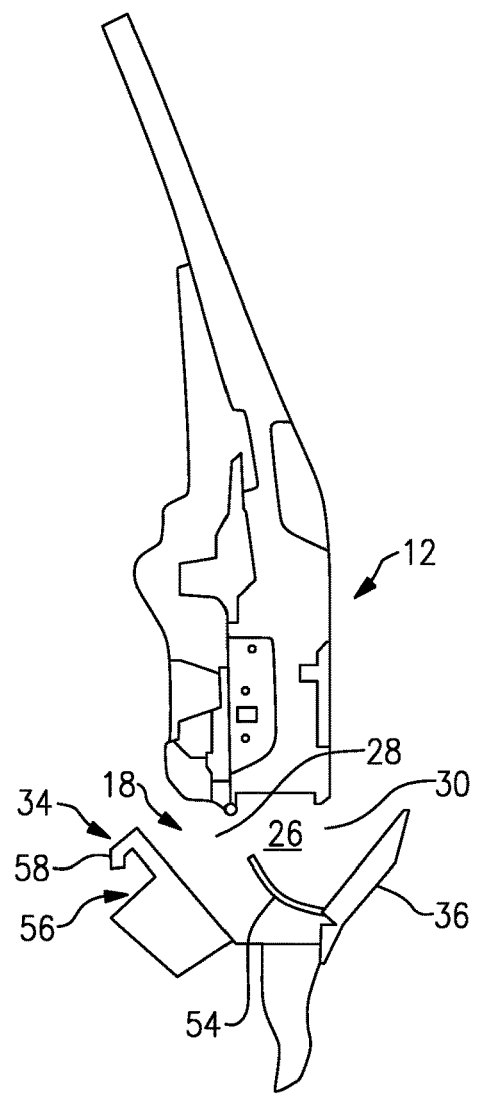
FIG. 6 is a cross-sectional of a vehicle door with another example storage bin.

FIG. 6 is view of another arrangement of the storage bin 18 with the inner and outer covers 34, 36 in an open position. In FIG. 6, the outer cover 36 includes a tray 54 connected to an inner surface of the outer cover 36 and arranged adjacent a bottom edge thereof. The tray 54 is configured to support an item placed in the storage bin 18 from the bottom, and increases the ease of inserting and retrieving items from persons on the exterior of the vehicle 10. Further, in this example, the inner cover 34 is incorporated into a piece of trim attached to the door 12. In particular, the inner cover 34 provides a storage compartment 56 facing toward the interior of the passenger compartment 16. Adjacent an upper edge thereof, the inner cover 34 includes a handle 58 such that a user can grasp the handle 58 to open the inner cover 34.

Figure 7:
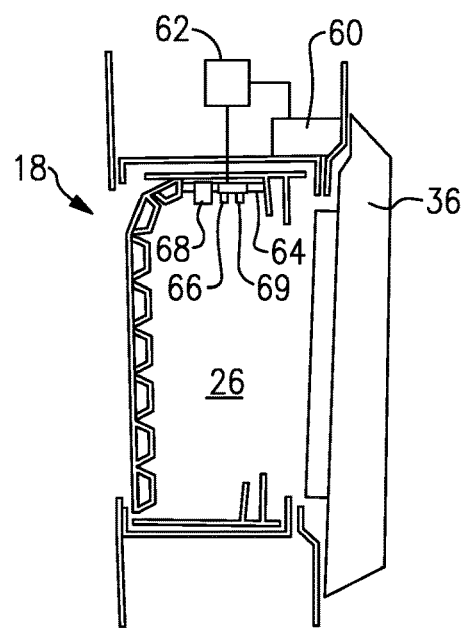
FIG. 7 is a cross-sectional view similar to FIG. 3, and illustrates additional detail of the storage bin.

In another aspect of this disclosure, the storage bin 18 is lockable in order to prevent unwanted access to the storage bin 18. Specifically, with reference to FIG. 7, the outer cover 36 is lockable in the closed position via a magnetic latch assembly 60. The magnetic latch assembly 60 is selectively activated in response to a command from a controller 62. When activated, the magnetic latch assembly 60 acts as a magnet and attracts the outer cover 36 so as to prevent the outer cover 36 from opening. The controller 62 is configured to deactivate the magnetic latch assembly 60 in response to an authorized command, such as a command from a delivery person, the vehicle owner, or another authorized user.

The controller 62 (sometimes called a "control unit") may be programmed with executable instructions for interfacing with and operating the various electromechanical components, including but not limited to those shown in the figures and discussed herein. It should also be understood that the controller 62 may include a combination of hardware and software, and specifically may include a processing unit and non-transitory memory for executing the various control strategies.

The storage bin 18 further includes a printed circuit board (PCB) 64, in this example. The controller 62 may be embodied on the PCB 64. The PCB 64 is mounted adjacent the top of the pass-through opening 26, and is mounted adjacent the trim piece 50 in this example. The PCB 64 may be an existing PCB, such as that used to control the powered aspects of the door 12, such as the windows, locks, etc.

Another aspect of this disclosure relates to disinfection of items placed in the storage bin 18. In particular, in FIG. 7, an ultraviolet (UV) light source 66 is arranged on the PCB 64 and is configured to emit UV light within the storage bin 18, namely within the pass-through opening 26. Specifically, the UV light source 66 is configured to emit UV light in response to a command from the controller 62. The controller 62 is configured, in one example, to cause the UV light source 66 to emit UV light for a predefined period of time, such as 30 seconds, when a new item is placed in the storage bin 18 to sanitize the item.

The UV light source 66 includes a UV-C bulb (sometimes called a "UV lamp"), such as a 13 Watt UV-C bulb configured to emit UV-C light. In other examples, the UV light source 66 is provided by a bulb within a range of 5 to 20 Watts. The UV light source 66 is configured to emit UV light having a wavelength within a range of 245-290 nanometers (nm) in one example, and in a specific example at a wavelength of wavelength of 254 nanometers (nm). UV-C light is a subtype of UV light especially suited for disinfection and is known to kill, break down, and/or inactivate microorganisms such as viruses, bacteria, germs, dust mites, mold, fungi, etc.

The storage bin 18 further includes a sensor 68, such as an infrared emitter, configured to generate a signal which can be interpreted by the controller 62 as being indicative of whether an item is present in the storage bin 18. The controller 62 can use the signal from the sensor 68 to initiate a number of actions, such as initiating the UV sanitization process discussed above. Additional exemplary actions will be discussed below.

The storage bin 18 may also include another light 69, such as an LED, configured to selectively emit light of a number of different colors and intensities so as to provide a status indication to a user. For instance, the light 69 could emit a green or blue light indicating that a UV sanitization cycle has been completed. The light 69 could emit a red light indicating that the UV sanitization cycle is ongoing and the inner and outer covers 34, 36 should not be opened. The light 69 could also indicate whether an item is present in the storage bin 18 and should be removed.

Further, the controller 62 can issue various messages to a user. As examples, the controller 62 can issue a message to a user indicative of an item having been placed in the storage bin 18 and/or having recently been sanitized. The message may be transmitted via a human-user interface 70 (FIG. 1) of the vehicle 10, such as a B-pillar applique or another display of the vehicle 10, or to a mobile device of the user via a transceiver 72, such as a Bluetooth or BLE (Bluetooth low energy) connection, of the vehicle 10, as examples. The human-machine interface 70 may include a speaker, such as a sound exciter, and a microphone such that a user can give live instructions to a delivery person and such that the delivery person can communicate with the user via the human-machine interface 70. The sound exciter could be incorporated into another panel of the vehicle 10 other than the B-pillar applique. The sound exciter is an electrical device that creates a vibration and is placed near a body panel of the vehicle 10 to create amplification for the sound.

When detecting that a new item is present in the storage bin 18, the controller 62 can also command a camera 74 of the vehicle 10 to take a photo and/or video of the area adjacent the storage bin 18 so a user can determine who placed the item in the storage bin 18, for example. The photo/video can be time stamped and stored for later viewing and/or transmitted to the user immediately. The camera 74 may be an existing camera, such as a camera configured for use with a self-driving system (SDS) of the vehicle 10.

Figure 8:
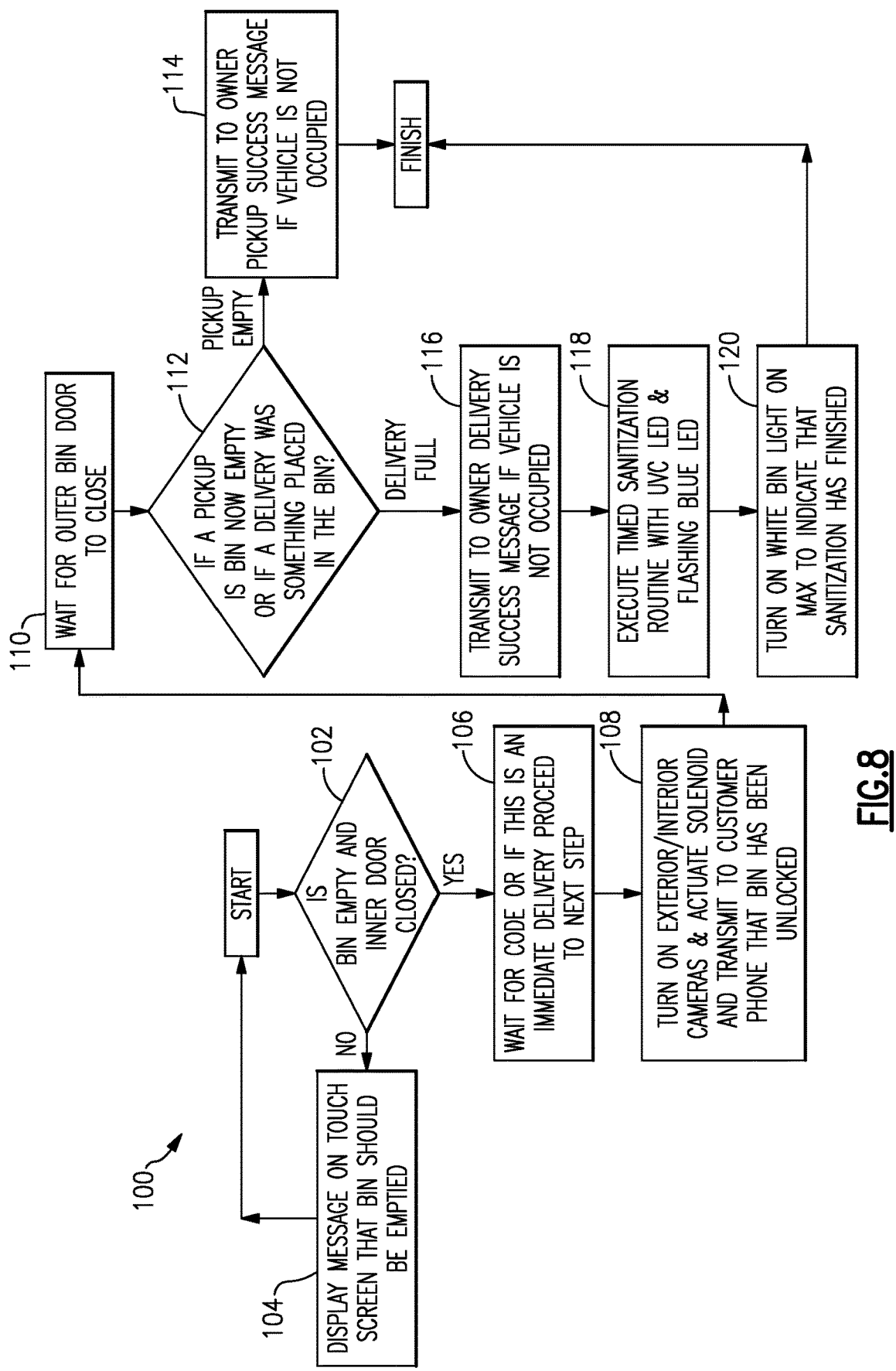
FIG. 8 is a flow chart representative of an example method.

FIG. 8 is a flow chart representative of an example method 100 of using the storage bin 18. Various additional aspects of the storage bin 18 and vehicle 10 will be described relative to FIG. 8. It should be understood that the components described and shown in FIGS. 1-6 are used to carry out the example method 100.

In the example, at 102, the controller 62 determines whether the storage bin 18 is empty and the inner cover 34 is closed. If not, then at 104 the controller 62 issues a message to the user, either via the human-machine interface 70 (i.e., the B-pillar applique) or via the transmitter 72, indicating the storage bin 18 should be emptied and the inner cover 34 should be closed. If the answer is yes, then at 106 the controller 62 activates the magnetic lock assembly 60 to hold the outer cover 36 in the closed position, and awaits input of an authorization code indicating that an individual has authorization to access the storage bin 18. The authorization code may be input via the human-machine interface 70 or by another technique, such as digital keys or codes offered by in-car delivery services such as Key by Amazon. In other examples, such as when the vehicle 10 is occupied, no authorization code is needed since the occupants of the vehicle 10 can monitor the storage bin 18 themselves. In such circumstances, the controller 62 deactivates the magnetic lock assembly 60 to readily permit access to the storage bin 18.

Upon receipt of an authorization code, at 108, the camera 74 begins recording, by taking one or more videos or photos, and a message is transmitted to the user/customer indicating that the storage bin 18 has been unlocked. At 110, when the storage bin 110 is again closed, the controller 62 determines whether the storage bin 18 is empty or whether an item is present in the storage bin 18 based on the signal from the sensor 68. The controller 62 can also compare the signal with a condition/instruction indicative of whether the user was expecting to receive a delivery or whether the user was arranging for a pickup of an item. If the user was expecting to arrange for a pickup and if the controller 62 determines that the storage bin 18 is now empty, them, at 114, the controller 62 issues a message to the user indicating that the pickup was successfully completed.

If, at 112, the user was expecting a delivery and if the controller 62 determines that the storage bin 18 now contains an item, then at 116 the controller 62 issues a message to the user indicating that the delivery was successfully completed. The controller 62 further begins the UV sanitization cycle, at 118, by activating the UV light source 66 and activating the light 69 a color indicative to a user that the UV sanitization cycle is ongoing. In an example, the light 69 flashes a blue color during the UV sanitization cycle. The light 69 is visible from the passenger compartment 16, in this example, such as when the inner cover 34 is partially transparent. The light 69 could be arranged elsewhere such that the user can readily view the light 69. Regardless, following the UV sanitization cycle, at 120, the light 69 turns a different color, which in this example is a constant (i.e., no longer flashing) white color, and/or a message is communicated to the user via the human-machine interface 70 and the transceiver 72 that the UV sanitization cycle has completed, at 120.

It should be understood that terms such as "about," "substantially," and "generally" are not intended to be boundaryless terms, and should be interpreted consistent with the way one skilled in the art would interpret those terms. It should also be understood that terms such as "outward," "inward," "front," "rear," "upward," "downward," etc., are used herein relative to the normal, upright operational attitude of the vehicle 10 for purposes of explanation only, and should not be deemed limiting.

Although the different examples have the specific components shown in the illustrations, embodiments of this disclosure are not limited to those particular combinations. It is possible to use some of the components or features from one of the examples in combination with features or components from another one of the examples. In addition, the various figures accompanying this disclosure are not necessarily to scale, and some features may be exaggerated or minimized to show certain details of a particular component or arrangement.

One of ordinary skill in this art would understand that the above-described embodiments are exemplary and non-limiting. That is, modifications of this disclosure would come within the scope of the claims. Accordingly, the following claims should be studied to determine their true scope and content.

The invention claimed is:

1. A motor vehicle, comprising:
a door providing a boundary between a passenger compartment of the motor vehicle and an exterior of the motor vehicle, wherein the door includes a storage bin configured such that an item in the storage bin is accessible both from the passenger compartment and from the exterior when the door is closed.

2. The motor vehicle as recited in claim 1, wherein:
the door includes an inner panel and an outer panel spaced-apart from the inner panel, and
the storage bin is at least partially between the inner panel and the outer panel.

3. The motor vehicle as recited in claim 2, wherein the storage bin includes a reinforcement assembly between the inner panel and the outer panel.

4. The motor vehicle as recited in claim 3, wherein the reinforcement assembly includes:
a bottom wall extending between the inner panel and the outer panel,
a top wall spaced-apart from the bottom wall and extending between the inner panel and the outer panel,
a forward wall extending between the inner panel and the outer panel and further extending between the bottom wall and the top wall, and
a rear wall spaced-apart from the forward wall and extending between the inner panel and the outer panel and further extending between the bottom wall and the top wall.

5. The motor vehicle as recited in claim 4, wherein the bottom wall, top wall, forward wall, and rear wall are provided by a single, integrally-formed assembly.

6. A motor vehicle, comprising:
a door providing a boundary between a passenger compartment of the motor vehicle and an exterior of the motor vehicle, wherein the door includes a storage bin configured such that an item in the storage bin is accessible both from the passenger compartment and from the exterior,
wherein the door includes an inner panel and an outer panel spaced-apart from the inner panel,
wherein the storage bin is at least partially between the inner panel and the outer panel,
wherein the inner panel includes an opening leading to the storage bin, and
wherein the outer panel includes an opening leading to the storage bin.

7. The motor vehicle as recited in claim 6, wherein the opening of the outer panel is at least partially aligned with the opening of the inner panel.

8. The motor vehicle as recited in claim 6, wherein:
the storage bin includes an inner cover moveable relative to the door to selectively cover and uncover the opening of the inner panel, and
the storage bin includes an outer cover moveable relative to the door to selectively cover and uncover the opening of the outer panel.

9. The motor vehicle as recited in claim 8, wherein:
the inner cover is biased toward a closed position in which the inner cover covers the opening of the inner panel by a first biasing member, and
the outer cover is biased toward a closed position in which the outer cover covers the opening of the outer panel by a second biasing member.

10. The motor vehicle as recited in claim 9, further comprising a lock configured to selectively lock the outer cover in the closed position.

11. The motor vehicle as recited in claim 8, wherein:
the inner cover is at least partially made of a transparent material such that contents of the storage bin are visible from the passenger compartment.

12. The motor vehicle as recited in claim 8, wherein:
the inner cover includes a sound absorbing panel, and
the outer cover includes a sound absorbing panel.

13. The motor vehicle as recited in claim 1, further comprising an ultraviolet (UV) light source configured to emit UV light within the storage bin to disinfect an item within the storage bin.

14. The motor vehicle as recited in claim 13, further comprising a controller configured to issue a command to the UV light source to selectively cause the UV light source to emit UV light.

15. The motor vehicle as recited in claim 14, wherein the controller is in communication with a sensor configured to generate a signal indicative of whether an item is present in the storage bin and is further configured to command the UV light source to emit UV light for a period of time following detection of an item in the storage bin.

16. The motor vehicle as recited in claim 15, wherein the controller is further configured to transmit a message indicative of one or both whether an item is present in the storage bin and whether the UV light has been activated for the period of time.

17. The motor vehicle as recited in claim 15, further comprising a printed circuit board mounted to the door adjacent the storage bin, and wherein the sensor, controller, and UV light source are mounted to the printed circuit board.

18. A method, comprising:
placing an item in a storage bin of a door of a motor vehicle by accessing the storage bin from an exterior of the motor vehicle when the door is closed; and
transmitting a message indicating an item is in the storage bin.

19. The method as recited in claim 18, further comprising:
sanitizing the item using UV light; and
retrieving the item, after the sanitizing step, from the storage bin by accessing the storage bin from a passenger compartment of the motor vehicle.

20. The method as recited in claim 19, wherein, after the sanitizing step and before the retrieving step, the message indicates that a sanitization process has completed.

* * * * *